United States Patent
Saito et al.

(10) Patent No.: US 8,390,815 B2
(45) Date of Patent: Mar. 5, 2013

(54) SURFACE TENSION MEASURING DEVICE AND METHOD

(75) Inventors: Takayuki Saito, Hamamatsu (JP);
Toshiyuki Sanada, Hamamatsu (JP);
Yusuke Ozawa, Hamamatsu (JP)

(73) Assignee: National University Corporation Shizuoka University (JP)

(*) Notice: Subject to any disclaimer, the term of this patent is extended or adjusted under 35 U.S.C. 154(b) by 482 days.

(21) Appl. No.: 12/667,184

(22) PCT Filed: Mar. 14, 2008

(86) PCT No.: PCT/JP2008/054789
§ 371 (c)(1),
(2), (4) Date: Dec. 29, 2009

(87) PCT Pub. No.: WO2009/004839
PCT Pub. Date: Jan. 8, 2009

(65) Prior Publication Data
US 2010/0188662 A1 Jul. 29, 2010

(30) Foreign Application Priority Data
Jun. 29, 2007 (JP) ................................. 2007-173513

(51) Int. Cl.
*G01N 21/55* (2006.01)
(52) U.S. Cl. .............. 356/445; 250/227.19; 250/227.27; 356/482; 356/502
(58) Field of Classification Search ........... 250/227.19–227.27; 356/445, 356/482, 502, 345, 357, 358
See application file for complete search history.

(56) References Cited

U.S. PATENT DOCUMENTS

| | | | | |
|---|---|---|---|---|
| 5,303,030 A | * | 4/1994 | Abraham et al. | 356/502 |
| 6,732,574 B2 | * | 5/2004 | Hajduk et al. | 73/54.05 |

FOREIGN PATENT DOCUMENTS

| | | |
|---|---|---|
| JP | 8-152396 | 6/1996 |
| JP | 2000-136962 A | 5/2000 |
| JP | 2004-286702 A | 10/2004 |
| JP | 2005-249696 A | 9/2005 |
| JP | 2006-226703 A | 8/2006 |

OTHER PUBLICATIONS

Tan'itsu Hikari Fiber Probe Keisoku ni Okeru Hyomen Choryoku to Nuresei no Eikyo, Nihon Konso Ryu Gakkai Noenkai Koen Ronbunshu, Jun. 22, 2007 vol. 2007, pp. 10-11.
Hikari Fiber Probe Sokutei ni Okeru Hyomen Choryoku no Eikyo, Abstract of Annual Meeting of the Society of Chemical Engineers, Japan, Feb. 19, 2007, vol. 72nd, p. 292.

* cited by examiner

*Primary Examiner* — Gregory J Toatley
*Assistant Examiner* — Iyabo S Alli
(74) *Attorney, Agent, or Firm* — McKee, Voorhees & Sease, P.L.C.

(57) ABSTRACT

Low-cost interface property measuring device and method enabling high-precision and simple measurement of an interface property. The interface property measuring device comprises an optical fiber probe (1) having a first end face (2) at least part of which is inclined with respect to a direction perpendicular to a fiber axis, a light supply (24) for supplying light from a second end face on the side opposite to the first end face of the optical fiber probe, a reflected light amount measuring device (24) for measuring the reflected light amount and a moving mechanism (18) for moving at least one of the optical fiber probe and an object (21) to be measured such that the first end face of the optical fiber probe passes through an interface (23) of the object (21) at a constant speed, and the interface property measuring device acquires the interface property of the object to be measured according to the result of measurement of the reflected light amount when the first end face of the optical fiber probe passes through the interface of the object to be measured.

12 Claims, 6 Drawing Sheets

FIG. 8

SURFACE TENSION MEASURING DEVICE AND METHOD

CROSS REFERENCE TO RELATED APPLICATIONS

This is a national stage application of PCT/JP2008/054789 filed on Mar. 14, 2008 which claims priority from Japanese application JP 2007-173513 filed on Jun. 29, 2007, all of which are incorporated herein by reference in their entirety.

BACKGROUND OF THE INVENTION

1) Field of the Invention

The present invention relates to a surface tension measuring device and method for measuring an interface property in an interface produced between air and a liquid or between different liquids, and more particularly for measuring surface tension.

2) Description of the Related Art

Surface tension is generated at the interface produced between air and a liquid or between different liquids. Surface tension is a fundamental physical property. The behavior of a liquid can be predicted by measuring the surface tension, which is an important physical parameter for industries involved with mixing, circulating, or otherwise handling liquids. Interface properties (wettability, interface contamination, and the like) related to surface tension are also important parameters.

A droplet method such as that disclosed in Patent Document 1 is a conventional method for measuring surface tension. This method involves observing droplets dropped from a narrow tube, but is not regarded to be simple because an image captured with a video camera is processed, and the pressure is controlled when a test material is drawn into the narrow tube in order to control the dropping of the droplets. Additionally, the sample to be measured must be introduced into the narrow tube and the amount of sample liquid inevitably increases. Furthermore, the narrow tube and other parts of the fluid supply system must be cleaned and there are many other disadvantages. Another conceivable method is one that uses an optical fiber as disclosed in Patent Document 2. This method is characterized in that a liquid sample material is deposited on the distal end of an optical fiber disposed in the optical path of a signal arm of a Michelson interferometer or another type of spectrointerferometer, and the physical properties of the liquid test material are measured from the interference signal obtained when there is interference between a reference light and a signal light reflected from the surface of the liquid test material. Similarly, this method cannot be regarded as simple because it requires a spectrointerferometer. Additionally, there is a drawback in this method in that a liquid with high surface tension such as water is difficult to uniformly deposit on an optical fiber.

Patent Documents 3 and 4 are prior art of the present inventors. These documents describe an air bubble detection probe for measuring the parallel speed, interface speed, air bubble chord length, and air bubble volume fraction using a fiber with an inclined distal end surface, but there is no description of measuring the surface tension at an interface. The interface deformation when the interface has made contact with the distal end of the fiber is regarded as negligible (paragraph 0011 of Patent Document 3) and consideration has not been given to the effect of surface tension.

Patent Document 1: Japanese Laid-open Patent Application No. H 8-152396
Patent Document 2: Japanese Laid-open Patent Application No. 2005-249696
Patent Document 3: Japanese Laid-open Patent Application No. 2000-136962
Patent Document 4: Japanese Laid-open Patent Application No. 2006-226703

SUMMARY OF THE INVENTION

The present invention was contrived in view of the problems of the prior art described above, and an object thereof is to provide a low-cost interface property measurement device and method enabling high-precision and simple measurement of an interface property, particularly the surface tension.

The present invention is constituted as follows in order to achieve the objects described above.

An interface property measuring device, comprising:
an optical fiber probe having a first end face at least part of which is inclined with respect to a direction perpendicular to a fiber axis;
light-supplying means for supplying light from a second end face on the side opposite to the first end face of the optical fiber probe;
reflected light amount measuring means for measuring the reflected light amount when the light supplied by the light-supplying means is reflected by the first end face and returned to the second end face; and
moving means for moving at least one of the optical fiber probe and an object to be measured so that the first end face of the optical fiber probe passes at a certain speed through an interface of the object to be measured, wherein
the interface property of the object to be measured is acquired according to the result of measurement of the reflected light amount when the first end face of the optical fiber probe passes through the interface of the object to be measured.

An interface property measuring method, using an optical fiber probe having a first end face at least part of which is inclined with respect to a direction perpendicular to a fiber axis, the method comprising:
a light-supplying step for supplying light from a second end face on the side opposite to the first end face of the optical fiber probe; and
a reflected light amount measuring step for measuring the reflected light amount when the light supplied in the light-supplying step is reflected by the first end face and returned to the second end face, wherein
the interface property of the object to be measured is acquired based on the result of measurement of the reflected light amount when the first end face of the optical fiber probe passes at a certain speed through the interface of the object to be measured.

Preferably, the following embodiments can be obtained. The interface property is surface tension. The interface property is acquired using at least the difference $\Delta t$ between the time at which the reflected light amount begins to increase or decrease and the time at which the reflected light amount becomes constant again. The interface property is acquired using the time rate of change of the reflected light amount $\Delta L/\Delta t$ (where $\Delta L$ is the difference in the reflected light amount before and after the first end face passes through the interface of the object to be measured). A thin film having high wettability is coated or vapor deposited on the first end face in order to increase the wettability of the first end face of the optical fiber probe. A surface structure is imparted to the first end face in order to increase the wettability of the first end face of the optical fiber probe. The moving means passes the optical fiber probe through the interface at a predetermined angle in order to promote the growth of a meniscus between the first end face and the interface when the first end face of the optical fiber probe makes contact with the interface of the object to be measured.

The interface property measuring device and method according to the present invention can measure an interface property; and the surface tension in particular, with high precision and in a simple manner by using the configuration described above. The dynamic surface tension and the static surface tension can be measured as the surface tension. It is also possible to measure wettability, interface contamination, and other interface properties related to surface tension. According to the present invention, cost reduction and simple operation can be achieved because the end face of an optical fiber is merely made to pass through the interface. In the case that the end face is contaminated or degraded, the distal end of the optical fiber can be cut away to reform an end face, resulting in an economical configuration, or the optical fiber can be readily replaced. Since the optical fiber is typically made of quartz, the fiber is resistant to corrosion and can be used to measure objects that are highly corrosive. The interface property is acquired from the change in reflectivity inside the optical fiber. Therefore, the interface property can be measured even for a liquid in which the object to be measured does not transmit light. It is possible to measure the interface property of the object even in a recessed or confined location because a narrow-diameter optical fiber probe is used.

As a result of experimentation, the present inventors found that an interface property; and the surface tension in particular, can be measured by measuring the behavior of the interface at the instant that the optical fiber probe, which has a inclined end face, makes contact with the interface by measuring the change in reflectivity (the reflected light amount) inside the optical fiber. In particular, the present inventors found that there is a fixed correlation between the surface tension and $\Delta t$ (the difference between the time at which the reflected light amount begins to increase or decrease and the time at which the reflected light amount becomes constant again), and that the surface tension can be measured using this relationship. With these new findings, the present invention makes it possible to measure an interface property; and the surface tension in particular, with high precision and more readily than with the prior art. The rate of meniscus growth can be increased and an interface property (surface tension) is more readily measured by performing a process that improves the wettability of the end face (first end face) of the optical fiber probe, even when the surface tension of the object to be measured is high and the probe end face is difficult to wet. Similarly, the meniscus growth speed can also be artificially increased between the interface of the object to the measured and the end face of the optical fiber probe by adjusting the entrance angle of the end face of the optical fiber probe in relation to the interface.

BRIEF DESCRIPTION OF THE DRAWINGS

FIG. 7(*a*) is a view of an example in which the optical fiber probe has entered perpendicularly with respect to the interface, and FIG. 7(*b*) is a view of an example in which the optical fiber probe has entered the interface at a fixed angle of incline.

DETAILED DESCRIPTION OF THE INVENTION

Figure 1:
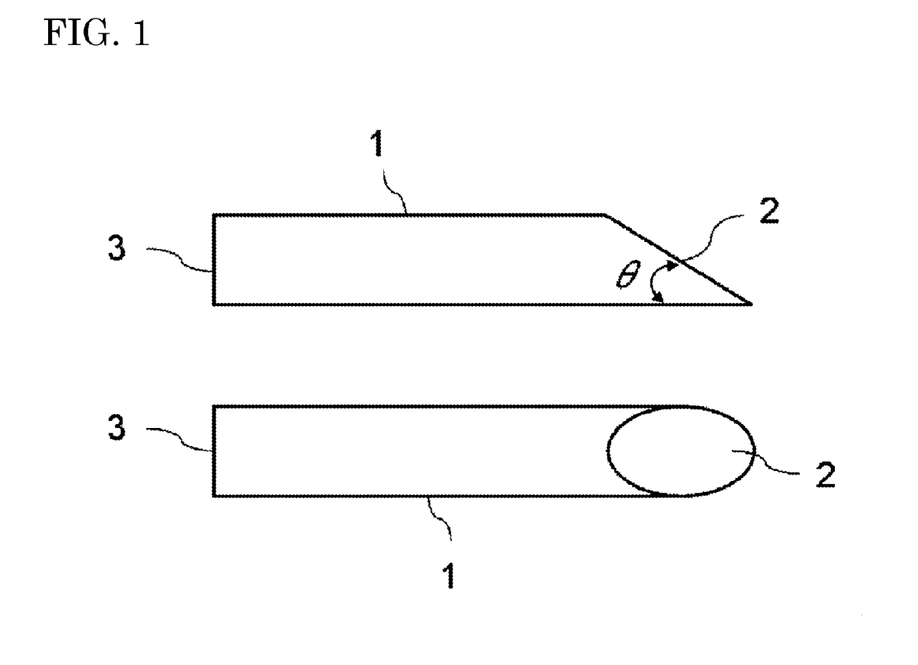
FIG. 1 shows the structure of an interface property-measuring optical fiber probe.

The preferred embodiments of the present invention are described below with reference to the attached drawings. The distal end of the optical fiber probe; i.e., the end face (first end face) in the interface detection end part for measuring an interface property used in the present embodiment, is formed so as to be inclined with respect to a direction perpendicular to a fiber axis, as shown in FIG. 1. The angle formed between the end face and the fiber axis is preferably an angle that efficiently reflects/refracts the light incident to the optical fiber at the end face with consideration given to the refractive index of the two substances constituting the interface of the object to be measured and to the refractive index of the core part of the optical fiber to be used. The angle does not depend on the diameter of the optical fiber to be used. The rear end of the optical fiber; i.e., the end face (second end face) in the light input/output part is preferably formed perpendicular to the fiber axis. According to the present embodiment, a laser light source can be used as the light source for supplying light to the end face inclined with respect to a direction perpendicular to the fiber axis. The light amount measuring means for measuring the light amount reflected from the end face may be any means that can measure the reflected light amount, examples of which include a photomultiplier, a phototransistor, and the like. The interface detection end face (first end face) is preferably in the shape shown in FIG. 1, but the shape is not limited to this shape as long as the shape has an inclined surface. For example, the end face may have a pointed conical shape or another shape.

The optical fiber probe according to the present embodiment passes through the interface of the object to be measured at a constant speed in a direction perpendicular to the interface. The light incident to the optical fiber reaches the optical fiber interface detection end face, and is reflected at the end face and returned inside the optical fiber. The reflected light amount varies in accordance with the refractive index of the substance covering the interface detection end face. Therefore, a difference is generated in the light amount reflected from the end face before and after the interface detection end face passes through the interface between substances having different refractive indices. Since the interface detection end face is inclined in a direction perpendicular to the fiber axis, the end face is gradually covered by the object to be measured when the end face passes through the interface, and the reflected light amount from the end face gradually increases or decreases. The contact process between the optical fiber probe and the interface when the optical fiber probe passes through the interface of the object to be measured varies in accordance with the surface tension of the object to be measured. Therefore, the time rate of change of the reflected light amount varies in accordance with the change in surface tension of the test object. In other words, the present invention is characterized in that the surface tension is obtained from variation in the time rate of change, which is caused by variation in the surface tension.

When the optical fiber interface detection end face passes through the interface of the object to be measured, the reflected light amount at the end face increases or decreases from a constant state and then becomes constant again. The time rate of change $g_{rd}$ of the reflected light amount is $g_{rd}=\Delta L/\Delta t$, where $\Delta t$ is the difference between the time at which the reflected light amount begins to increase or decrease and the time at which the reflected light amount becomes constant again, and $\Delta L$ is the difference in the reflected light amount before and after the end face passes through the interface. The surface tension is computed using a calibration curve and the time rate of change $g_{rd}$ obtained in the manner described above. The calibration curve is produced by measuring in advance a reagent for which the surface tension is known using the optical fiber probe according to the present embodiment. The surface tension can thereby be measured using the present optical fiber probe. The computations described above can be carried out using a personal computer or other known computation means.

The $\Delta L$ is determined by the shape of the distal end of the optical fiber probe, the refractive index of the object to be measured, and other factors, and since the parameter that depends greatly on the surface tension is $\Delta t$, the surface tension can be computed using only $\Delta t$. The transition curve at the instant the reflected light amount changes can be measured as long as the reflected light amount measuring means and the computation means has time to do so, and the surface tension can be obtained from the transition curve.

An embodiment according to the present invention will be described in detail with reference to the drawings. FIG. 1 shows the structure of an interface property-measuring optical fiber, which has an end face inclined with respect to a direction perpendicular to the fiber axis, wherein the top portion is a side view and the bottom portion is a plan view. The reference numeral 1 in the drawing is an interface property measuring optical fiber, and in the present example, the distal end of the interface property-measuring optical fiber 1; i.e., the interface detection end face (first end face) 2, is formed so that the angle θ formed by the interface detection end face 2 and the fiber axis is 35°. On the other hand, the rear end of the interface property-measuring optical fiber 1; i.e., the light input/output end face (second end face) 3, is formed so that the angle formed by the light input/output end face 3 and the fiber axis is 90°. According to the present example, the diameter of the interface property-measuring optical fiber 1 is about 230 μm.

Figure 2:
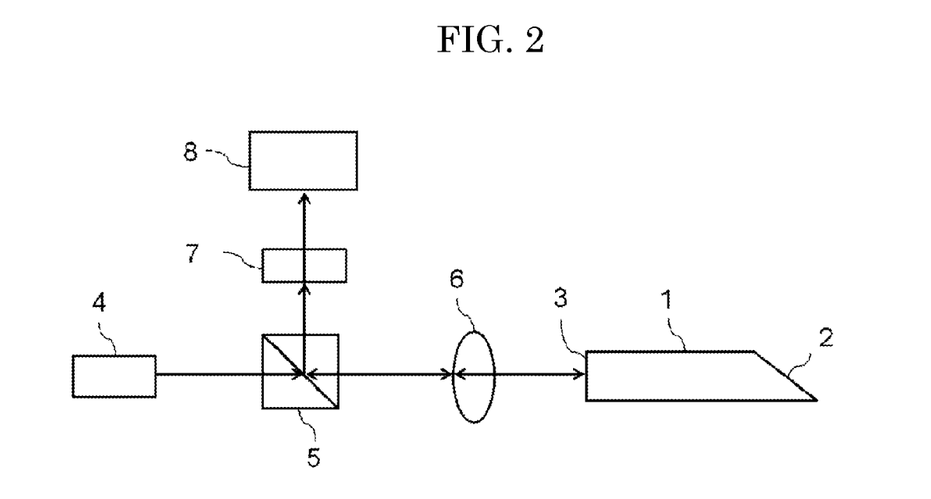
FIG. 2 is a schematic view according to an embodiment in which light is introduced from a light source to the interface property-measuring optical fiber probe and the light reflected from the interface detection end face is measured.

For example, as shown in FIG. 2, the light emitted from the light source 4 is passed through a beam splitter 5, focused by a lens 6, and passed from the rear end 3 into the interface property-measuring optical fiber 1 until it arrives at the distal end 2 of the optical fiber. The light that has arrived at the distal end 2 is reflected at the end face of the distal end 2, returned into the optical fiber, passed through the lens 6, redirected by the beam splitter 5, and passed through a polarizer 7 for removing scattered light before entering the photomultiplier 8, at which point the amount of light is measured.

Figure 3:
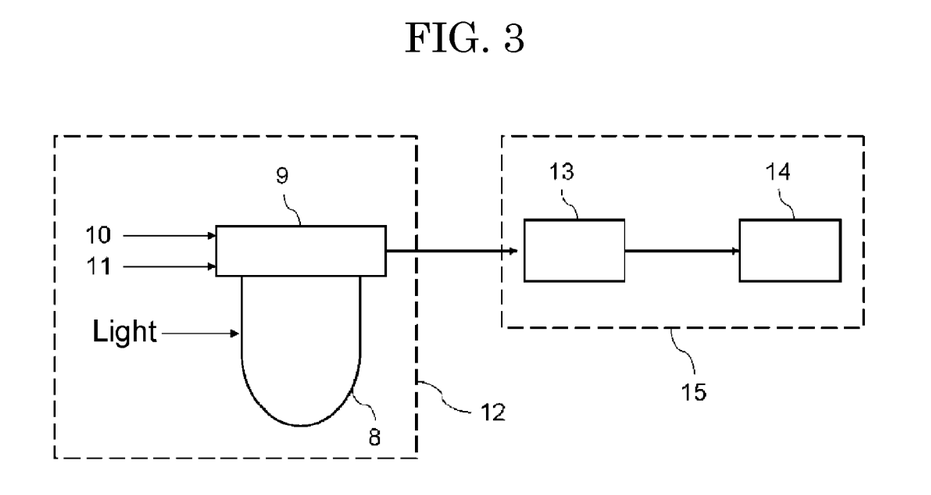
FIG. 3 is a schematic block view of the signal processing system for the reflected light amount measured by the interface property-measuring optical fiber probe.

FIG. 3 shows a schematic block diagram of an example of the signal processing system for the measured amount of light according to the present invention. The signal processing system is composed of a light-amount measuring device 12 having a photomultiplier 8, an output amplifier, a high-voltage DC circuit 9, an amplifier power source 10, and a DC voltage 11; and a computation device 15 having an A/D converter 13 and a personal computer 14.

Figure 4:
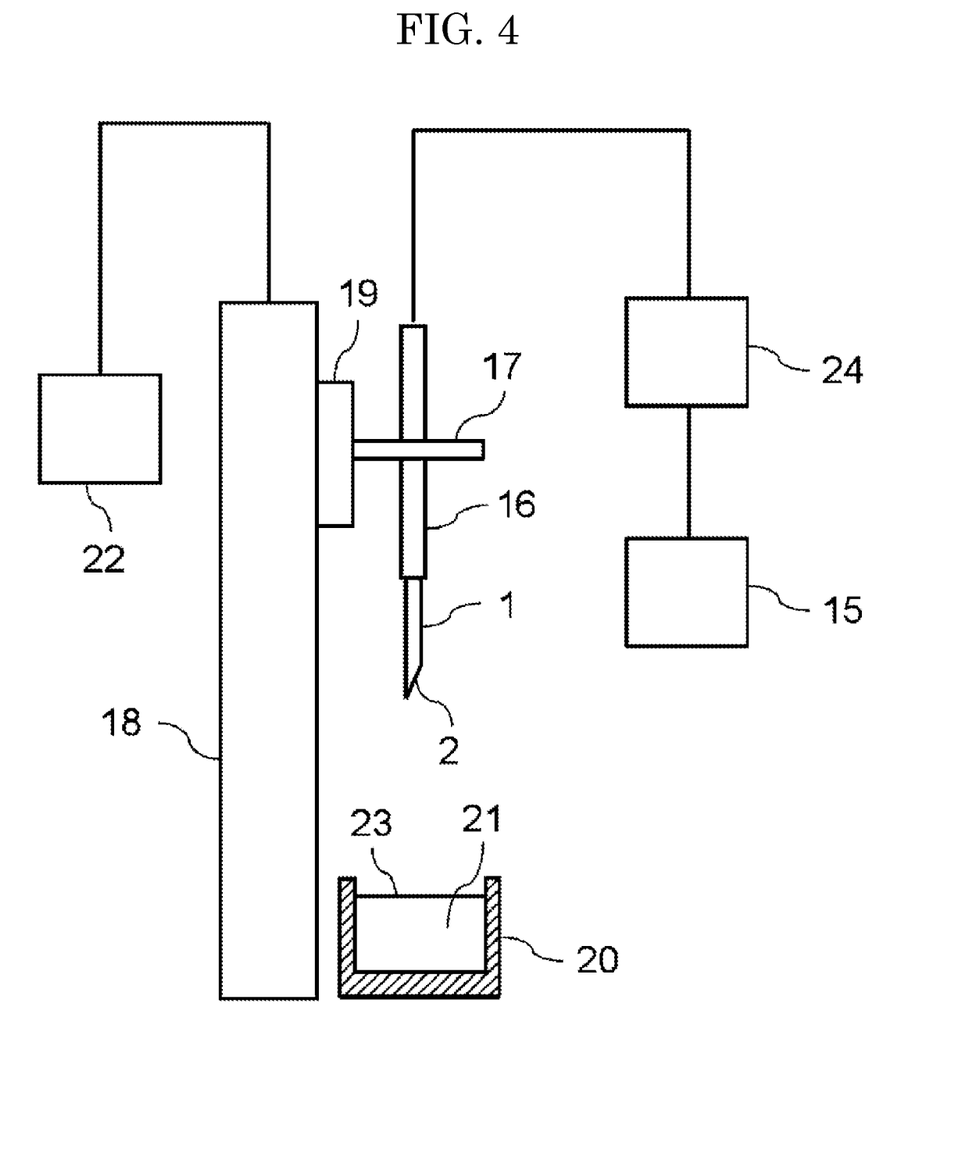
FIG. 4 is a schematic view of the measuring device for measuring interface properties.

FIG. 4 shows a schematic view of the interface property-measuring device according to the present invention. The interface property-measuring optical fiber 1 is secured inside a narrow tube 16 preferably made of stainless steel and set on a sliding table 19 of an automatic stage 18 using a securing jig 17. An object 21 to be measured is arranged directly below the interface property-measuring optical fiber 1, loaded in a container 20. An automatic stage control device 22 is operated, the interface detection end face 2 of the interface property-measuring optical fiber 1 is passed through the interface 23 of the object to be measured, and the surface tension is measured. Reference numeral 24 in the drawing is a light-introduction and light-amount-measuring system, and reference numeral 15 is a computation device. According to the present example, the interface-property-measuring optical fiber 1 is moved, but the interface of the object to be measured may be moved instead.

Figure 5:
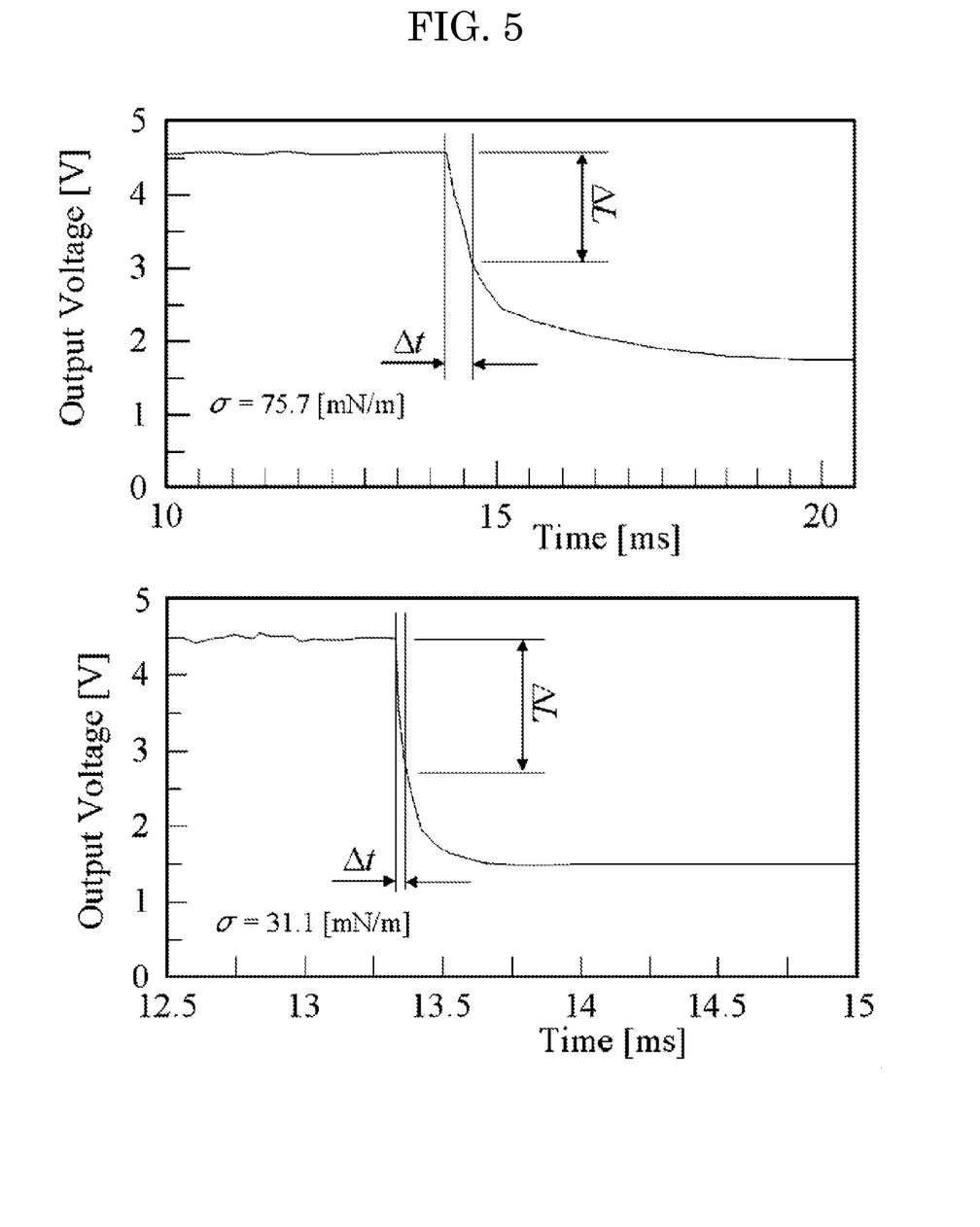
FIG. 5 is an example of the reflected light amount measured by the interface property-measuring optical fiber probe.
Figure 6:
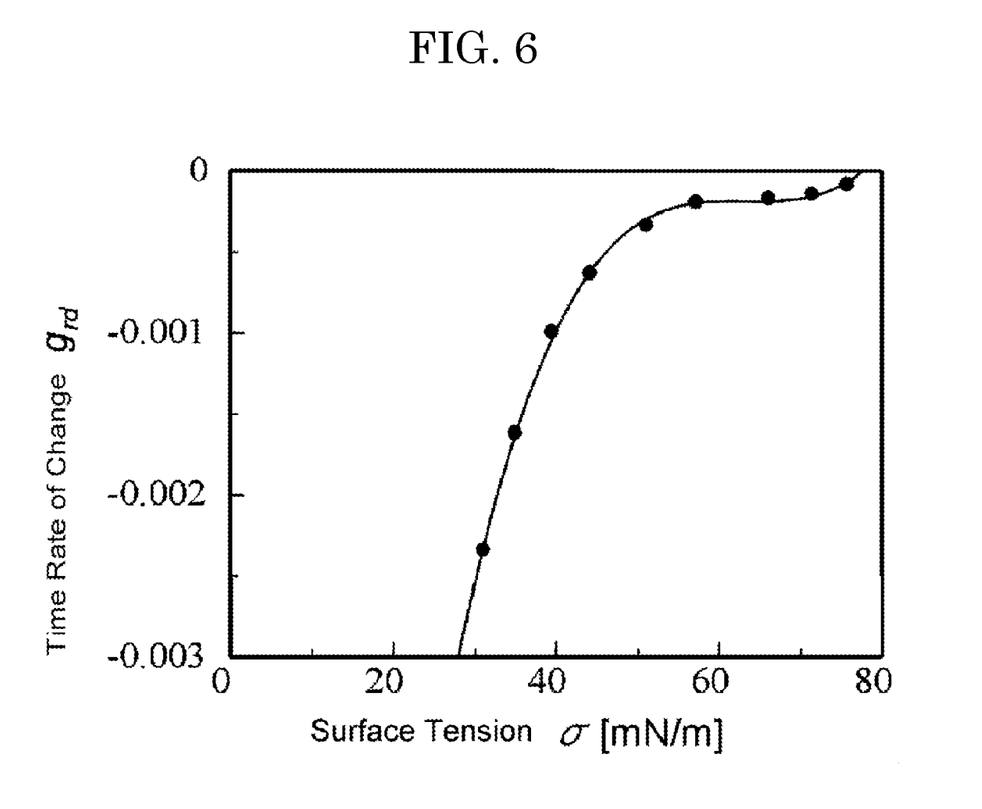
FIG. 6 is a view showing the relationship between the rate of change over time of the reflected light amount and the surface tension when the interface detection end face of the interface property-measuring optical fiber probe passes through the interface of the object to be measured.

Next, an example of an experiment and measurement according to the present invention will be described. In the experiment, an optical fiber probe having an end face inclined at an angle θ of 35° was manufactured using a quartz optical fiber having an outside diameter of 230 μm and a core part refractive index of 1.46. A semiconductor laser having a wavelength of 635 nm and a maximum output of 3 mW was used as the light source inputted to the probe. The surfactant 1-pentanol, which was the object to be measured, was gradually added to pure water and the surface tension was varied. The temperature was 20°. The relationship between the 1-pentanol concentration and the surface tension is shown in Table 1. The inclined end face of the present optical fiber probe was passed through the interface of the object to be measured at a constant speed of 100 units. As a result, a difference was generated (in the drawing, a represents the surface tension) in the time rate of change $g_{rd}$ (=$\Delta L/\Delta t$) of the output signal, as shown in FIG. 5. FIG. 6 shows an example of the relationship between the surface tension and the time rate of change $g_{rd}$. This is used as a calibration curve and the surface tension can be computed by calculating the time rate of change $g_{rd}$ of the output signal.

TABLE 1

Concentration of 1-pentanol and surface tension (20° C.)

| 1-pentanol concentration [ppm] | 0 | 500 | 1200 | 2500 | 4500 | 7000 | 10000 | 14000 | 18000 |
|---|---|---|---|---|---|---|---|---|---|
| Surface tension [mN/m] | 75.7 | 71.4 | 66.1 | 57.2 | 51.1 | 44.2 | 39.5 | 35.0 | 31.1 |

Figure 7:
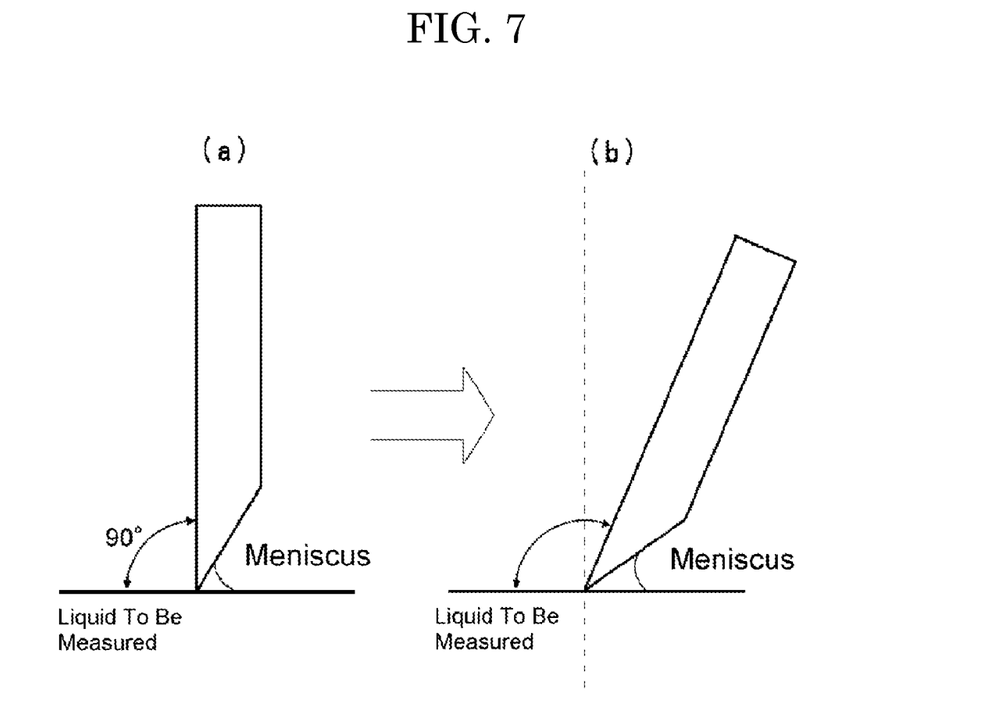

In FIG. 6, the variation in the time rate of change $g_{rd}$ of the output signal in relation to the surface tension reduces when the surface tension is about 55 mN/m or greater. This is due to the fact that the distal end part of the probe becomes more difficult to wet and the growth speed of the meniscus on the probe distal end face is reduced when the surface tension is high. As a result, the time rate of change $g_{rd}$ is reduced in relation to the surface tension. As a countermeasure, the growth speed of the meniscus can be increased. Methods for solving this include (1) applying or vapor-depositing a thin film having high wettability on the end face of the distal end part of the optical fiber probe (e.g., using UV rays to photoexcite a photocatalyst coating of titanium dioxide, form a hydroxyl group, and generate a coating with high wettability); (2) imparting pores, concavities and convexities, or other surface structures to the end face of the distal end part of the optical fiber probe to increase the wettability (e.g., the probe end face is ground using a diamond plate, a very short pulse laser is directed onto the end face, and microgrooves are formed parallel to the optical axis of the fiber (width: several hundred nanometers, depth: several hundred nanometers)); and (3) and reducing the angle between the interface and the inclined surface of the distal end of the optical fiber probe to artificially increase the growth speed of the meniscus (although this depends on the magnitude of the surface tension, the angle formed between the interface and the inclined face of the distal end of the probe can be set to, e.g., about 10° to 30° (angle formed by the interface and the center axis of the probe: about 45° to 65°) in the case that the surface tension is 55 mN/m to 80 mN/m.). FIG. 7 relates to method (3) described above. In the experiment described above, the optical fiber probe was made to enter perpendicular with respect to interface, as shown in FIG. 7(a), however, the angle between the interface and the inclined face of the distal end of the optical fiber probe is reduced and the growth speed of the meniscus can be artificially increased by tilting the optical fiber probe, as shown in FIG. 7(b).

Figure 8:
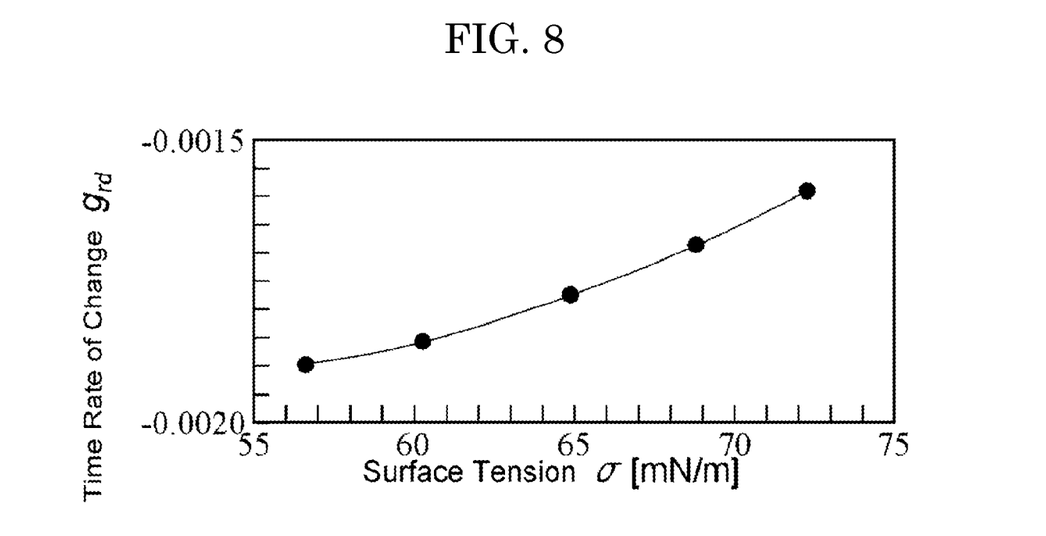
FIG. 8 a view showing the relationship between the rate of change over time of the reflected light amount and the surface tension when the interface detection end face of the interface property-measuring optical fiber probe passes through the interface of the object to be measured at the contact angle of FIG. 7(*b*).

FIG. 8 shows the experimental results of the relationship between the time rate of change $g_{rd}$ of the output signal and the surface tension σ when the distal end of the optical fiber probe makes contact with the interface at the contact angle (angle formed by the interface and the inclined face of the probe distal end: 15°; angle formed by the interface and the center axis of the probe: 50°) shown in FIG. 7(b). In FIG. 6, variation in the time rate of change $g_{rd}$ with respect to the surface tension σ is reduced when the surface tension σ is about 55 mN/m or higher, and it is difficult to compute the surface tension σ from the time rate of change $g_{rd}$, but in FIG. 8, the amount of increase in the time rate of change $g_{rd}$ with respect to the surface tension σ is sufficient, and the surface tension σ can be computed from the time rate of change $g_{rd}$. Therefore, the meniscus growth speed can be artificially increased by adjusting the contact angle of the distal end of the optical fiber probe in relation to the interface, the detection accuracy of the time rate of change $g_{rd}$ can be increased, and the surface tension σ can be measured more accurately, even in the case that the surface tension σ is high and variation in the time rate of change $g_{rd}$ is difficult to detect.

An embodiment of the present invention was described above, but the present invention is not limited thereto. It shall be apparent that various modifications can be made within the scope of the technical concepts described in the claims. In the embodiment described above, measurements were principally taken of the surface tension, but it is possible to measure additional interface properties related to the surface tension; e.g., wettability, interface contamination, and the like.

The invention claimed is:

1. An surface tension measuring device, comprising:
    an optical fiber probe having a first end face, at least part of which being inclined with respect to a direction perpendicular to a fiber axis;
    light-supplying means for supplying light from a second end face on the side opposite the first end face of the optical fiber probe;
    reflected light amount measuring means for measuring the reflected light amount when the light supplied by the light-supplying means is reflected by the first end face and returned to the second end face; and
    moving means for moving at least one of the optical fiber probe and an object to be measured so that the first end face of the optical fiber probe passes at a constant speed through an interface of the object to be measured, wherein
    the surface tension of the object to be measured is acquired based on the time change of the reflected light amount when the first end face of the optical fiber probe passes through the interface of the object to be measured.

2. The surface tension measuring device according to claim 1, wherein the surface tension is acquired at least using the difference Δt between the time at which the reflected light amount begins to increase or decrease and the time at which the reflected light amount becomes constant again.

3. The surface tension measuring device according to claim 2, wherein the surface tension is acquired using the time rate of change of the reflected light amount ΔL/Δt (where ΔL is the difference in the reflected light amount before and after the first end face passes through the interface of the object to be measured).

4. The surface tension measuring device according claim 1, wherein a thin film having high wettability is applied to or vapor-deposited on the first end face in order to increase the wettability of the first end face of the optical fiber probe.

5. The surface tension measuring device according to claim 1, wherein a surface structure is imparted to the first end face in order to increase the wettability of the first end face of the optical fiber probe.

6. The surface tension measuring device according to any of claims 1 and 2-5, wherein the moving means passes the optical fiber probe at a predetermined angle through the interface of the object to be measured in order to promote the growth of a meniscus between the first end face of the optical fiber probe and the interface when the first end face makes contact with the interface.

7. An interface property measuring device, comprising:
an optical fiber probe having a first end face, at least part of which being inclined with respect to a direction perpendicular to a fiber axis;
light-supplying means for supplying light from a second end face on the side opposite the first end face of the optical fiber probe;
reflected light amount measuring means for measuring the reflected light amount when the light supplied by the light-supplying means is reflected by the first end face and returned to the second end face; and
moving means for moving at least one of the optical fiber probe and an object to be measured so that the first end face of the optical fiber probe passes at a constant speed through an interface of the object to be measured, wherein
the interface property related to the surface tension of the object to be measured is acquired based on the time change of the reflected light amount when the first end face of the optical fiber probe passes through the interface of the object to be measured.

8. A surface tension measuring method, using an optical fiber probe having a first end face, at least part of which being inclined with respect to a direction perpendicular to a fiber axis, the method comprising:
a light-supplying step for supplying light from a second end face on the side opposite the first end face of the optical fiber probe; and
a reflected light amount measuring step for measuring the reflected light amount when the light supplied by the light-supplying step is reflected by the first end face and returned to the second end face, wherein
the surface tension of an object to be measured is acquired based on the time change of the reflected light amount when the first end face of the optical fiber probe passes at a constant speed through an interface of the object to be measured.

9. The surface tension measuring method according to claim 8, wherein the surface tension is acquired at least using the difference $\Delta t$ between the time at which the reflected light amount begins to increase or decrease and the time at which the reflected light amount becomes constant again.

10. The surface tension measuring method according to claim 9, wherein the surface tension is acquired using the time rate of change of the reflected light amount $\Delta L/\Delta t$ (where $\Delta L$ is the difference in the reflected light amount before and after the first end face passes through the interface of the object to be measured).

11. The surface tension measuring method according to any of claims 8-10, wherein the optical fiber probe is passed at a predetermined angle through the interface of the object to be measured in order to promote the growth of a meniscus between the first end face of the optical fiber probe and the interface when the first end face makes contact with the interface.

12. An interface property measuring method, using an optical fiber probe having a first end face, at least part of which being inclined with respect to a direction perpendicular to a fiber axis, the method comprising:
a light-supplying step for supplying light from a second end lace on the side opposite the first end thee of the optical fiber probe; and a reflected light amount measuring step for measuring the reflected light amount when the light supplied by the light-supplying step is reflected by the first end face and returned to the second end face, wherein an interface property related to the surface tension of the object to be measured is acquired based on the time change of the reflected light amount when the first end face of the optical fiber probe passes at a constant speed through the interface of the object to be measured.

* * * * *

UNITED STATES PATENT AND TRADEMARK OFFICE
CERTIFICATE OF CORRECTION

PATENT NO. : 8,390,815 B2
APPLICATION NO. : 12/667184
DATED : March 5, 2013
INVENTOR(S) : Takayuki Saito et al.

Page 1 of 1

It is certified that error appears in the above-identified patent and that said Letters Patent is hereby corrected as shown below:

In the Claims:

Col. 10, Claim 12, Line 24:
DELETE before on "lace"
ADD before on --face--

Col. 10, Claim 12, Line 24:
DELETE before of "thee"
ADD before of --face--

Col. 10, Claim 12, Line 29:
DELETE after wherein "an"
ADD after wherein --the--

Signed and Sealed this
Ninth Day of July, 2013

Teresa Stanek Rea
*Acting Director of the United States Patent and Trademark Office*